(12) United States Patent
Burkert

(10) Patent No.: US 10,722,428 B2
(45) Date of Patent: Jul. 28, 2020

(54) STERILE CONTAINER COMPRISING STERILE BARRIER SEPARATE FROM PRIMARY PACKAGE AND METHOD OF MANUFACTURING STERILE CONTAINER

(71) Applicant: B. BRAUN AVITUM AG, Melsungen (DE)

(72) Inventor: Sina Burkert, Dresden (DE)

(73) Assignee: B. BRAUN AVITUM AG, Melsungen (DE)

(*) Notice: Subject to any disclaimer, the term of this patent is extended or adjusted under 35 U.S.C. 154(b) by 358 days.

(21) Appl. No.: 15/692,092

(22) Filed: Aug. 31, 2017

(65) Prior Publication Data

US 2018/0078457 A1    Mar. 22, 2018

(30) Foreign Application Priority Data

Sep. 19, 2016  (DE) .......................... 10 2016 117 599

(51) Int. Cl.
| | | |
|---|---|---|
| *A61J 1/18* | (2006.01) | |
| *A61M 1/16* | (2006.01) | |
| *B65B 55/20* | (2006.01) | |
| *B65B 55/16* | (2006.01) | |
| *B65B 23/00* | (2006.01) | |
| *B65B 55/19* | (2006.01) | |

(Continued)

(52) U.S. Cl.
CPC ................ *A61J 1/18* (2013.01); *A61J 1/1481* (2015.05); *A61M 1/1682* (2014.02); *B29C 66/0018* (2013.01); *B29C 66/53245* (2013.01); *B65B 23/00* (2013.01); *B65B 55/16* (2013.01); *B65B 55/19* (2013.01); *B65B 55/20* (2013.01); *A61M 2209/06* (2013.01); *B65B 55/12* (2013.01); *B65B 2220/16* (2013.01)

(58) Field of Classification Search
CPC ......... A61J 1/18; A61J 1/1481; A61M 1/1682
USPC ........................................................ 604/403
See application file for complete search history.

(56) References Cited

U.S. PATENT DOCUMENTS

| | | |
|---|---|---|
| 5,015,374 A | 5/1991 | Mathieu et al. |
| 6,315,895 B1 | 11/2001 | Summerton et al. |

(Continued)

FOREIGN PATENT DOCUMENTS

| | | |
|---|---|---|
| DE | 3825573 A1 | 2/1990 |
| DE | 60033058 T2 | 6/2007 |
| DE | 102014108530 A1 | 12/2015 |

OTHER PUBLICATIONS

German Search Report for German Application No. 10 2016 117 599.4, with partial translation, dated Apr. 3, 2017—13 Pages.

(Continued)

*Primary Examiner* — Andrew J Mensh

(57) ABSTRACT

A sterile container including at least one hollow fiber filter module, especially dialyzer, which is accommodated in a hermetically sealed holding volume of a primary package and includes a blood compartment delimited by a blood inlet opening and a blood outlet opening, wherein a plurality of hollow fiber filter modules is arranged in the primary package and the sterile barrier of the blood compartment of each hollow fiber filter module inside the primary package is implemented by caps which close the blood inlet opening and the blood outlet opening of each hollow fiber filter module. A method of manufacturing such sterile container is also disclosed.

12 Claims, 3 Drawing Sheets

(51) Int. Cl.
*A61J 1/14* (2006.01)
*B29C 65/00* (2006.01)
*B65B 55/12* (2006.01)

(56) References Cited

U.S. PATENT DOCUMENTS

| | | | | |
|---|---|---|---|---|
| 2001/0023232 | A1 | 9/2001 | McKedy | |
| 2003/0196949 | A1* | 10/2003 | Sunohara | A61M 1/16 210/321.71 |
| 2005/0063859 | A1* | 3/2005 | Masuda | A61M 1/16 422/44 |
| 2010/0193387 | A1* | 8/2010 | Sato | A61L 2/087 206/438 |
| 2012/0318727 | A1* | 12/2012 | Kawatani | B01D 63/02 210/321.89 |
| 2013/0105337 | A1* | 5/2013 | Williams | A61F 17/00 206/210 |
| 2015/0359958 | A1 | 12/2015 | Kaestner | |

OTHER PUBLICATIONS

European Search Report for European Application No. 17187517.2, with partial translation, dated Jan. 3, 2018—15 Pages.

\* cited by examiner

STERILE CONTAINER COMPRISING STERILE BARRIER SEPARATE FROM PRIMARY PACKAGE AND METHOD OF MANUFACTURING STERILE CONTAINER

CROSS REFERENCE TO RELATED APPLICATIONS

This application claims priority to German application DE 10 2016 117 599.4 filed Sep. 19, 2016, the contents of such application being incorporated by reference herein.

FIELD OF THE INVENTION

The invention relates to a sterile container comprising at least one hollow fiber filter module, especially a dialyzer, which is accommodated in a hermetically sealed holding volume of a primary package and includes a blood compartment delimited by a blood inlet opening and a blood outlet opening which are in the form of a Luer connection, for example. Moreover, the invention relates to a method of producing or manufacturing a sterile container, especially such sterile container according to aspects of the invention as set forth by the present description or by any one of the attached claims.

BACKGROUND OF THE INVENTION

Requirements to a package for a medical product are defined in numerous standards. Especially a package for sterile medical products is subjected to strict regulations. In the case of hollow fiber filter modules, for example dialyzers, the standard EN ISO 8637:2014 "Cardiovascular implants and extracorporeal systems—hemodialyzers, hemodiafilters, hemofilters and hemoconcentrators" is especially important and has to be complied with. With respect to the sterility of packaged hollow fiber filter modules, this standard defines the fact that blood-conveying parts of the apparatus have to be sterile and consequently have to be properly packaged. Related to a hollow fiber filter module such as a dialyzer, this means that the blood compartment of the module has to be sterile, whereas the dialysate compartment is subjected to less strict requirements.

For sterilizing packaged hollow fiber filter modules the use of gamma rays within the scope of radiation is generally known. Gamma ray sterilization takes place in the absence of oxygen so as to avoid oxidative material stress both of the packaged hollow fiber filter module and of the package used for this purpose during sterilization. In known sterile containers for hollow fiber filter modules one module at a time is packaged together with one oxygen absorber in a primary package hermetically sealed against the ambience. The oxygen absorber is put into the primary package (special package consisting of polyamide and polyethylene), thus causing oxygen to be almost completely removed from the medical product and from the interior of the package. Around the oxygen absorber and the packaged hollow fiber filter module, the primary package forms a hermetically sealed envelope surrounding and defining a holding volume in which almost no oxygen is present any more as a result of the oxygen absorption. In this condition, the sterilization by means of gamma radiation takes place. A plurality of primary-packaged and sterilized units, for example a lot size of 20, then is accommodated in a secondary package. It can be stated that the secondary package then contains 20 tightly packaged and sterile hollow fiber filter modules (dialyzers). The primary package defines the volume to be sterilized during sterilization and thus forms a sterile barrier which represents the barrier between a sterile and a non-sterile compartment.

The afore-described concept according to prior art involves great challenges: On the one hand, it has to be ensured that before and during sterilization the volume to be sterilized is free from oxygen. On the other hand, it has to be ensured that after sterile packaging, during transport and during the entire storage (usually up to 3 years) of the containers up to the ultimate use the sterility of the hollow fiber filter module is safeguarded. In the afore-described known sterile containers it is a drawback that by improper transport and/or storage the sensitive primary package can be minimally perforated, for example when the primary packages including the filter modules accommodated therein are rubbing against each other in a secondary package. Perforation of the primary package prior to sterilization may result in the fact that oxygen diffuses from outside into the package and is present during sterilization. In this way, the material can be stressed by oxidation. In the case of perforation after sterilization a non-sterility may occur inside the holding volume of the primary package and thus of the dialysate compartment of the filter module. It is another drawback of known packaging concepts that an additional oxygen absorber always has to be added to each individual filter module packaged in a primary package.

Other packaging concepts are known, for example by means of deep-drawn packages made from a strong special film adapting to the shape of a filter module or using alternative films available on the market. Another known solution in which sterilization is equally performed by means of radiation with gamma rays makes use of a tight aluminum-coated package. A drawback in these concepts consists in high cost and production expenditure.

Based on the afore-described prior art, the object underlying the present invention is to eliminate the afore-listed drawbacks, especially to provide a technical concept by which the risk of perforation of the sterile barrier by improper transport and storage can be reduced and thus the sterility of the product can be ensured even in the case of improper transport and/or improper storage.

SUMMARY OF THE INVENTION

According to aspects of the invention, this object is achieved by a sterile container comprising at least one hollow fiber filter module such as a dialyzer which is accommodated in a hermetically sealed holding volume of a primary package and includes a blood compartment delimited by a blood inlet opening and a blood outlet opening. The invention excels by the fact that in the primary package a plurality of hollow fiber filter modules is arranged and the sterile barrier of the blood compartment of each hollow fiber filter module inside the primary package is implemented by caps such as protection caps which close the blood inlet opening and the blood outlet opening of the respective hollow fiber filter module. With respect to a method, the object is achieved by a method of producing a sterile container, especially according to any one of the attached claims or according to the present description, wherein a plurality of hollow fiber filter modules, especially dialyzers, is arranged in a primary package, the primary package then is closed while forming a hermetically sealed holding volume, oxygen present in the closed holding volume is absorbed by means of an oxygen absorber, subsequently sterilization takes place by means of gamma radiation and the primary package including the hollow fiber filter modules packaged therein is introduced to a secondary package.

It is a particular advantage of the invention that the primary package comprising plural hollow fiber filter modules/dialyzers each including a blood compartment and a dialysate compartment is not equivalent to the sterile barrier. So, according to aspects of the invention, the sterile barrier is exclusively configured by the protection caps covering the two blood connections, i.e. the blood inlet opening and the blood outlet opening, both being preferably in the form of Luer connections. Said protection caps are robust against perforations, which has a positive effect on the sterility of the container over the service life thereof. Furthermore, it is resulting from this configuration that the compartment to be kept sterile has a considerably smaller volume than before, thus helping to increase the efficiency of sterilization in terms of time and profitability. From the fact that, according to aspects of the invention, plural dialyzers are enclosed by one single primary package which seals the dialyzers hermetically, namely, in an air-tight manner, against the ambience, plural advantages will be resulting. For, when in one single primary package plural dialyzers are contained, there is substantially no portion of the primary package provided between the dialyzers, which is why damage such as perforations by movements of the dialyzers packaged in the sterile container relative to each other can be largely prevented, at least reduced as compared to prior art. Furthermore, the surface of the primary package formed according to aspects of the invention is definitely smaller than the surfaces of plural primary packages according to prior art for an equal number of filter modules.

Advantageous embodiments of the invention are claimed in the subclaims and will be illustrated in detail hereinafter.

It is of advantage when the closing caps/protection caps/caps are non-positively connected/friction-locked/connected via a frictional connection to the blood inlet opening and, respectively, to the blood outlet opening. When the respective openings are in the form of Luer openings and, respectively, Luer connections, the force fit can be easily and reliably realized by means of a Luer lock. As an alternative to the non-positive connection, mainly positive attachment of the closing caps is of advantage. In this context, clipping, crimping or mounting is appropriate.

In another advantageous embodiment, the primary package is in the form of a puncture-proof film so as to prevent perforations from being introduced to the primary package. Such film excels by high ductility as compared to common films as they are used, for example, in prior art for primary packages. According to one embodiment of the invention, the primary package is also formed by a flexible film. Due to its flexibility, it can properly adapt to the shape of the filter modules packaged therein. The film is intended to ensure that the package is free from oxygen at least during sterilization. Preferably, it is moreover hermetically sealed over a quite long period, for example over one to three years, so that the package is free from oxygen even over such period. In a case in which after sterilization oxygen nevertheless migrates through the film in the course of a quite long period of time, this is no drawback as long as sterility is safeguarded by means of the protection caps, as an oxygen-free state has no reducing effect on the quality of a once sterilized product.

As soon as an oxygen absorber has been introduced to the primary package or to the holding volume so as to avoid oxidative material stress, the sterilization can be reliably executed so that at the end thereof undesired microorganisms are removed. The fact that, according to aspects of the invention, a primary package contains plural dialyzers entails another advantage in that, instead of having to provide a separate oxygen absorber for each individual filter module, only one single oxygen absorber has to be used for the plurality of filter modules. This facilitates handling and manufacturing operations during the manufacture of the sterile container.

As an alternative or in addition, the oxygen absorber may be integrated in the puncture-proof film, hence the primary package may be formed by an oxygen-absorbing film. In particular, an oxygen-absorbing film already being in use in the food industry may be used. By making use of adequately large oxygen absorbers or a film having sufficient capacity a most tight package can be produced, which strongly reduces the impact contacts among the dialyzers. That is to say, the atmospheric oxygen is removed, the package contracts and strongly compresses the dialyzers.

Another advantage results from the primary package being contracted due to oxygen absorption by the oxygen absorber, especially being contracted so that it is adjacent to the hollow fiber filter modules/dialyzers disposed in the same and fixes the latter against each other. In this way, similar to the use of a shrink film, a relatively firm packaging container is produced in which the filter modules packaged in the primary package are adjacent to each other and to the primary package so that each module inside the packaging compound has a relatively stable position. Mutual displacement of the filter modules relative to each other and to the primary package thus can be largely avoided in an advantageous manner. In this way, the probability of perforation of the primary package is additionally reduced, while the perforation of the sterile barrier continues to be excluded. With respect to the method according to aspects of the invention, it can be stated that the holding volume of the primary package is reduced due to oxygen absorption such that the hollow fiber filter modules accommodated therein are fixed in a stable position by contact with the primary package and/or by mutual contact.

Another embodiment of the invention is in the holding volume between at least part of the hollow fiber filter modules an intermediate layer, for example in the form of cardboard, film, air bubble film or foam pad, is interposed. Such intermediate layers may advantageously suppress, at least restrict, movements of the filter modules relative to each other. Thus, they serve not only for protecting the packaged filter modules but in addition for protecting the primary package in that they can avoid perforations due to movements of the filter modules. The intermediate layers may be arranged to be plane-parallel to each other or else to intersect each other.

According to another embodiment, the primary package may be surrounded by a secondary package which is in the form of a firm receptacle, especially formed by a cardboard box. The use of different materials such as wood or plastic or metal is within the scope of the invention.

Between the secondary package and the primary package an intermediate layer, for example in the form of cardboard, film, air bubble film or foam pad, may be arranged so as to dampen impacts acting on the dialyzers. Apart from impacts, by means of said intermediate layer also vibrations possibly acting from outside on the sterile container do not affect the sterile barrier or else the primary package. The arrangement of the dialyzers present in the primary package may be vertical or horizontal in the secondary package. This means that the secondary package can be filled from above or from the side.

With respect to the method according to aspects of the invention, in one embodiment the sterilization takes place after introducing the primary package including the hollow fiber filter modules/dialyzers packaged therein to the secondary package. In this way, an especially proper protection of the primary package is achieved during sterilization.

It can also be stated that the invention provides an alternative packaging concept in which an oxygen-absorbing material is used for producing a most tight package of plural hollow fiber filter modules, especially dialyzers, on the way to sterilization while complying with all regulations for dialyzers. In a first option, a film comprising an additional oxygen absorber is used. In a second option, a special film comprising an integrated oxygen absorber is used. Both options may be combined. According to aspects of the invention, a film which is very thick and puncture-proof as compared to common packaging films can be used for the primary packaging. Additional flexible intermediate layers may be used which further reduce disturbing impact effects.

Especially the following advantages and improvements can be brought about by the invention:
- facilitating sterilization and maintaining the same by reason of the smaller sterile compartment and by reason of the robust protection caps;
- risk-minimizing measure for preventing perforations in the primary package;
- risk-minimizing measure for preventing destruction of the sterile barrier;
- avoiding risks for a patient in the case of improper transport of the filter modules;
- cheaper than known concepts, as a primary package including an oxygen absorber is not provided for each filter module/each dialyzer but for the respective plurality, for example 20 items, packaged in the primary package.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
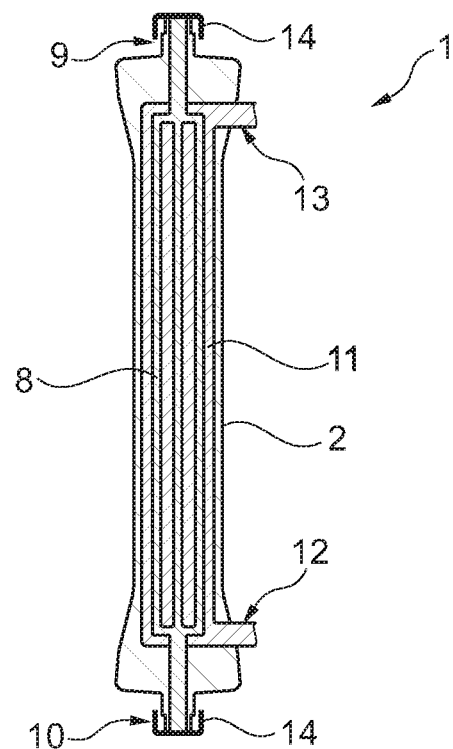
FIG. 1 shows a dialyzer comprising a blood inlet opening and a blood outlet opening each being closed by a protection cap.

FIG. 1 illustrates part of a sterile container 1 according to aspects of the invention. This part is composed of a dialyzer 2 and two protection caps 14. The one protection cap 14 is attached to a blood inlet opening 9, the other protection cap 14 is attached to a blood outlet opening 10. The blood inlet and blood outlet openings 9, 10 are provided extending in the longitudinal direction of the dialyzer 2 at two opposite ends of the dialyzer 2.

Between the openings 9, 10 a blood compartment 8 is defined. The latter is sealed in a sterile manner by the protection caps 14. While a medium to be dialyzed, preferably blood, is supplied to the blood compartment 8 via the blood inlet opening 9, which is in the form of a Luer connection, said medium exits the blood compartment via the blood outlet opening 10. In the counter flow principle, a dialysate is supplied to a dialysate compartment 11 via a dialysate inlet opening 12 and is removed from the dialysate compartment 11 via a dialysate outlet opening 13.

The blood openings 9, 10 are arranged to extend in the longitudinal direction of the dialyzer 2, while the dialysate openings 12, 13 are arranged to be angled hereto.

The force fit between the protection caps 14 and the openings 9, 10 is preferably configured via a Luer lock.

Figure 2:
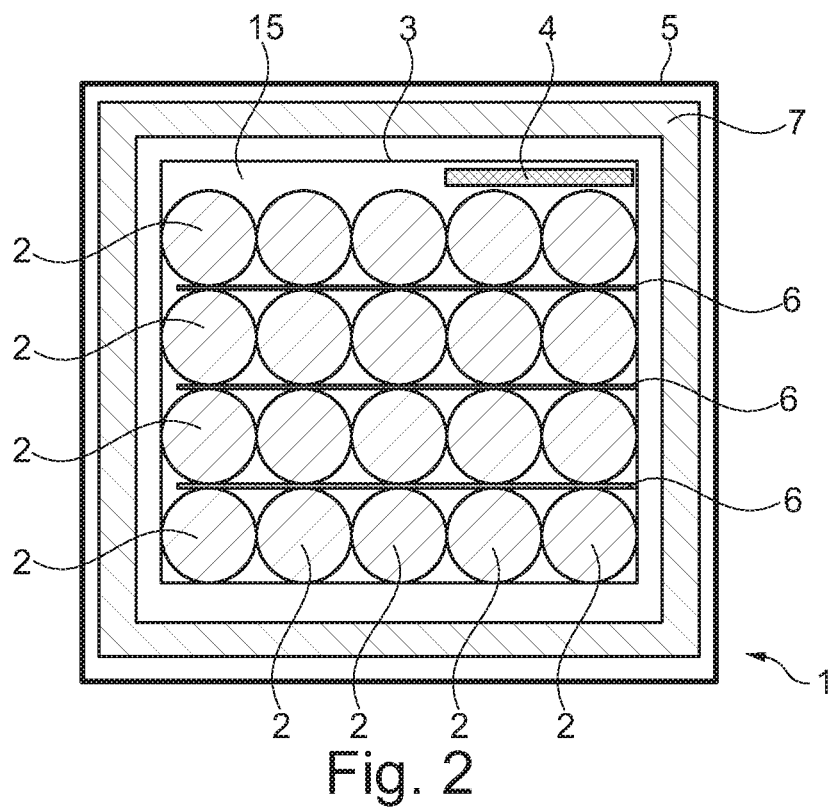
FIG. 2 shows a first embodiment of the invention in a schematic representation.
Figure 3:
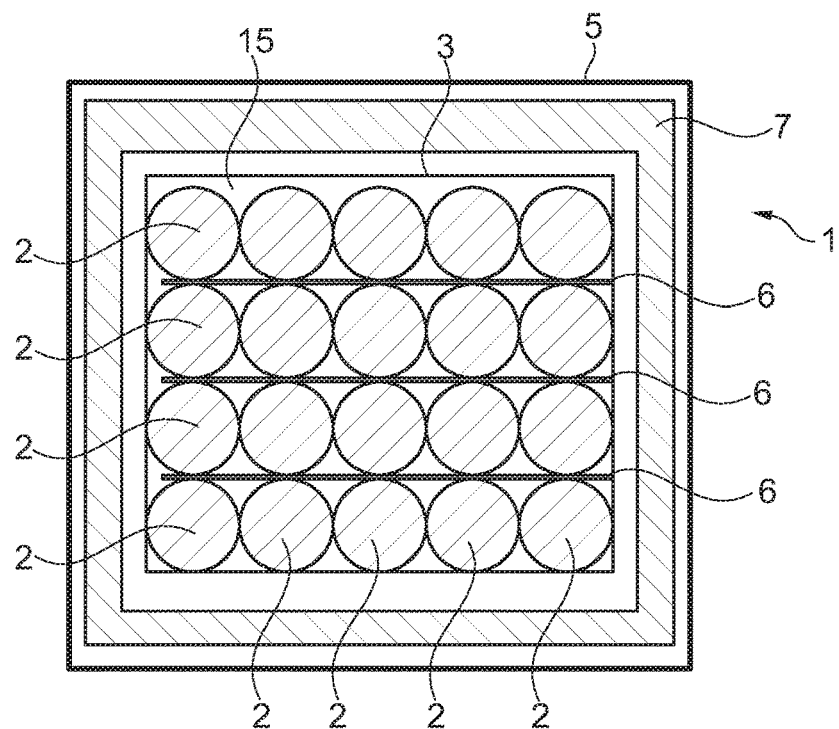
FIG. 3 shows a second embodiment of the invention in a schematic representation.
Figure 4:
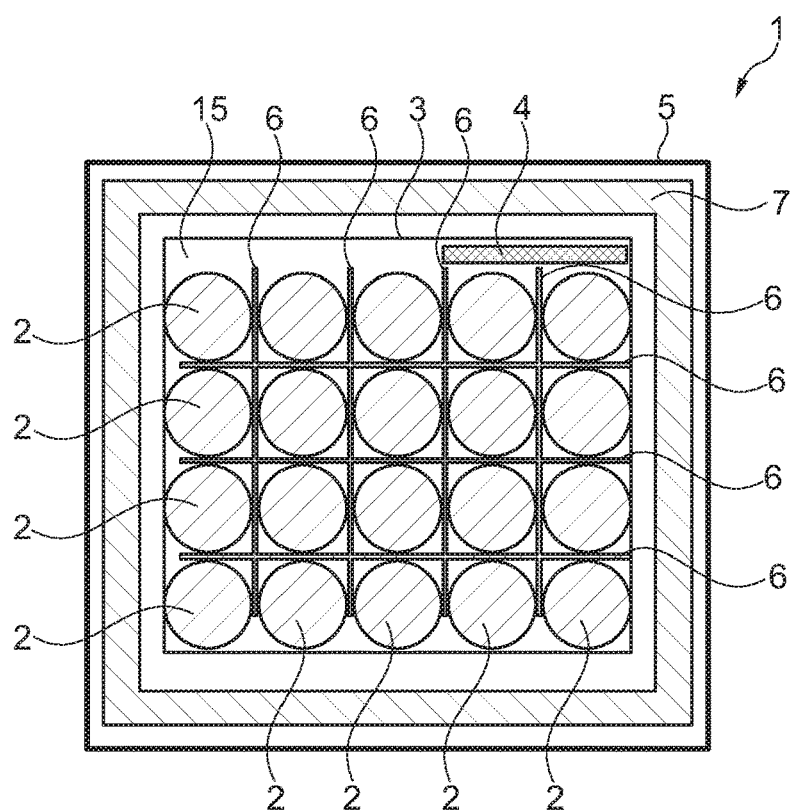
FIG. 4 shows a third embodiment of the invention in a schematic representation.
Figure 5:
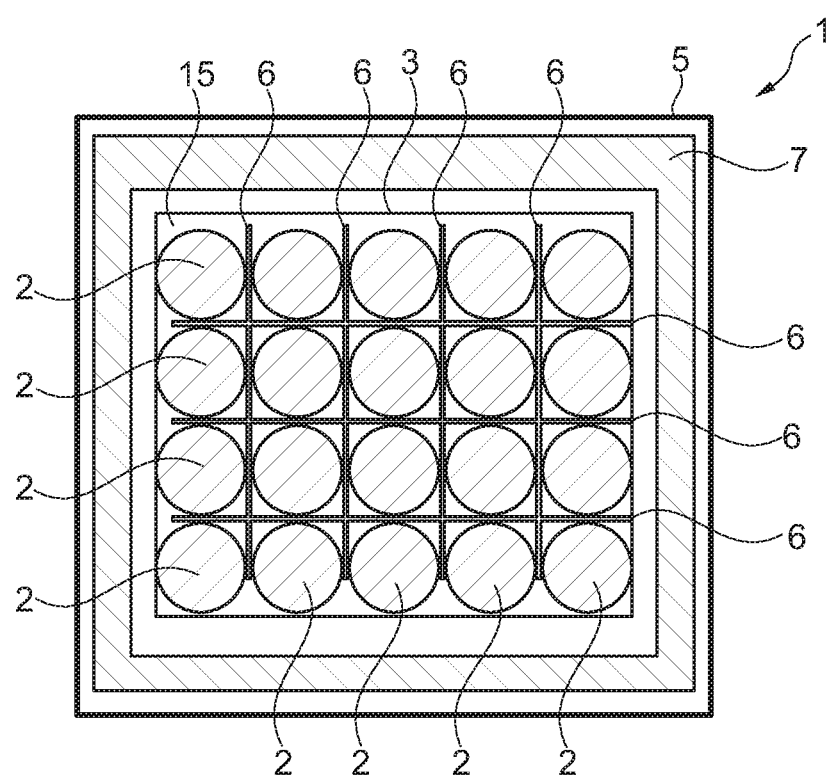
FIG. 5 shows a fourth embodiment of the invention in a schematic representation.

FIGS. 2 and 3 describe a concept according to aspects of the invention taking into consideration that cardboard boxes 5 (secondary packages 5) are filled from above. The dialyzers 2 are so-to-speak placed next to each other. In the embodiment of FIGS. 4 and 5, the dialyzers 2 are put into a pre-fabricated flexible padding net forming an intermediate layer 6 (similarly to a wine package), i.e. they are standing upright. A boundary layer to neighboring dialyzers 2 is formed to all directions. The sterile barrier is realized via the protection caps 14 between the afore-shown blood compartment 8 and the holding volume 15 formed by the primary package 3.

FIGS. 2 to 5 moreover show that in a primary package 3 a plurality of dialyzers 2 is accommodated. In the shown case, one single primary package 3 contains twenty dialyzers 2 which are arranged in four rows each including five dialyzers 2.

The primary package 3 of the embodiments of the FIGS. 2 and 3 are formed of flexible films, for example made from polyamide and/or polyethylene. In said embodiments one oxygen absorber 4 is provided and arranged in each primary package 3, i.e. one single absorber 4 for twenty filter modules 2. Between each of the four rows of dialyzers 2 the intermediate layer 6 or the intermediate bottom 6 is disposed. Moreover, between the primary package 3 and the secondary package 5 an intermediate pad 7 is arranged in the form of an air or foam pad 7 which prevents or at least inhibits impacts, jolts and vibrations from being transmitted from the secondary package 5 to the primary package 3.

The primary packages 3 of the embodiments of the FIGS. 3 and 5 are made from flexible films which per se have oxygen-absorbing properties. Especially, said films are oxygen-absorbing films that have been used already in the food industry. Between the four rows of dialyzers 2 a cross-shaped or matrix-shaped net of intermediate layers 6 or intermediate bottoms 6 is arranged such that each mutual contact of dialyzers 2 is suppressed. Moreover, between the primary package 3 and the secondary package 5 an intermediate pad 7 is arranged in the form of an air or foam pad 7 which prevents or at least inhibits impacts, jolts and vibrations from being transmitted from the secondary package 5 to the primary package 3.

Due to the fact that, in accordance with the invention, the sterile barrier is realized by the protection caps 14, one oxygen absorber 4 is used for all dialyzers 2 in a secondary package 5. According to aspects of the invention, the number of dialyzers 2 in the secondary package 5 corresponds to the number of dialyzers 2 in the primary package 3.

The invention claimed is:
1. A sterile container comprising:
  a primary package having a hermetically sealed holding volume;
  a plurality of hollow fiber filter module accommodated in the hermetically sealed holding volume, each of the plurality of hollow fiber filter modules including: a blood compartment delimited by a blood inlet opening and a blood outlet opening, and respective caps including a respective first cap which closes the blood inlet opening and a respective second cap which closes the blood outlet opening to form a sterile barrier for the blood compartment.

2. The sterile container according to claim 1, wherein at least one of the first cap is connected to the blood inlet opening or the second cap is connected to the blood outlet opening via a frictional connection.

3. The sterile container according to claim 1, wherein the primary package is in the form of a puncture-proof film that prevents perforations from being introduced to the primary package.

4. The sterile container according to claim 3, wherein an oxygen absorber is introduced to the primary package or to the holding volume so as to avoid oxidative material stress.

5. The sterile container according to claim 4, wherein the oxygen absorber is integrated in the puncture-proof film.

6. The sterile container according to claim 4, wherein the primary package is contracted due to oxygen absorption by the oxygen absorber and is adjacent to the plurality of hollow fiber filter modules disposed therein so as to fix the plurality of hollow fiber filter modules against each other.

7. The sterile container according to according to claim 1, wherein an intermediate layer is interposed in the holding volume between at least two of the plurality of hollow fiber filter modules.

8. The sterile container according to according to claim 1, further comprising:

a secondary package in the form of a container surrounding the primary package, the secondary package being relatively firm as compared to the primary package.

9. The sterile container according to claim 8, further comprising:

an intermediate pad interposed between the secondary package and the primary package to dampen impacts acting on the plurality of hollow fiber filter modules.

10. The sterile container according to claim 1, wherein each of the plurality of hollow filter modules is a dialyzer.

11. A method of producing a sterile container according to claim 1, the method comprising:

arranging the plurality of hollow fiber filter modules in the primary package;

closing the primary package while forming the hermetically sealed holding volume;

absorbing oxygen present in the closed holding volume with an oxygen absorber;

sterilizing the closed primary package using gamma radiation; and introducing the primary package including the hollow fiber filter modules packaged therein to a secondary package.

12. The method according to claim 11, wherein the holding volume of the primary package is reduced due to the oxygen absorption so that the hollow fiber filter modules accommodated therein are fixed in a stable position by at least one of contacting the primary package or by mutual contact.

* * * * *